US012048579B2

United States Patent
Koyanagi

(10) Patent No.: US 12,048,579 B2
(45) Date of Patent: Jul. 30, 2024

(54) RADIATION IMAGING SYSTEM AND CABLE USED THEREFOR

(71) Applicant: CANON KABUSHIKI KAISHA, Tokyo (JP)

(72) Inventor: Takahiro Koyanagi, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 134 days.

(21) Appl. No.: 17/697,021

(22) Filed: Mar. 17, 2022

(65) Prior Publication Data

US 2022/0302658 A1  Sep. 22, 2022

(30) Foreign Application Priority Data

Mar. 17, 2021  (JP) ................................. 2021-043774

(51) Int. Cl.
*A61B 6/00* (2024.01)
*A61B 6/42* (2024.01)
*A61B 6/04* (2006.01)

(52) U.S. Cl.
CPC .............. *A61B 6/56* (2013.01); *A61B 6/0407* (2013.01); *A61B 6/4208* (2013.01); *A61B 6/4283* (2013.01)

(58) Field of Classification Search
CPC ......... H01R 13/73; A61B 6/0407; A61B 6/42; A61B 6/56; A61B 6/4283; A61B 6/4208
See application file for complete search history.

(56) References Cited

U.S. PATENT DOCUMENTS

| 6,855,936 B2 | 2/2005 | Yamamoto |
| 8,956,045 B2 | 2/2015 | Tajima et al. |
| 9,072,485 B2 | 7/2015 | Tajima et al. |
| 9,282,939 B2 | 3/2016 | Tajima et al. |
| 10,156,641 B2 | 12/2018 | Hiratsuka et al. |
| 2003/0042418 A1 | 3/2003 | Yamamoto |

(Continued)

FOREIGN PATENT DOCUMENTS

| JP | 2003-144424 A | 5/2003 |
| JP | 2010-259680 A | 11/2010 |

(Continued)

OTHER PUBLICATIONS

Computerized English translation of JP 2017-060632 A (Mar. 30, 2017). (Year: 2017).*

*Primary Examiner* — Chih-Cheng Kao
(74) *Attorney, Agent, or Firm* — VENABLE LLP

(57) ABSTRACT

The radiation imaging system includes a cable configured to transmit at least one of a signal and power from an external apparatus, a connector portion provided in an end of the cable, a radiation imaging apparatus, and an imaging table, the radiation imaging apparatus being attachable to and removable from the imaging table, wherein the radiation imaging apparatus includes a rectangular-shaped housing configured to contain a radiation detecting panel, a housing-side connection terminal portion is arranged in a side surface of the housing, the housing-side connection terminal portion is capable to be connected with the connector portion, and the connector portion includes at least one penetrating hole penetrating from a front surface parallel to a radiation incident surface to a rear surface opposite to the front surface, the penetrating hole being usable for fixation to the imaging table.

14 Claims, 5 Drawing Sheets

(56) References Cited

U.S. PATENT DOCUMENTS

| | | |
|---|---|---|
| 2012/0250823 A1 | 10/2012 | Vogtmeier et al. |
| 2013/0083898 A1 | 4/2013 | Tajima et al. |
| 2015/0146864 A1 | 5/2015 | Tajima et al. |
| 2015/0257723 A1 | 9/2015 | Tajima et al. |

FOREIGN PATENT DOCUMENTS

| | | | |
|---|---|---|---|
| JP | 2015-62687 A | | 4/2015 |
| JP | 2016-197584 A | | 11/2016 |
| JP | 2017-60632 A | | 3/2017 |
| TW | 201824658 A | * | 7/2018 |

* cited by examiner

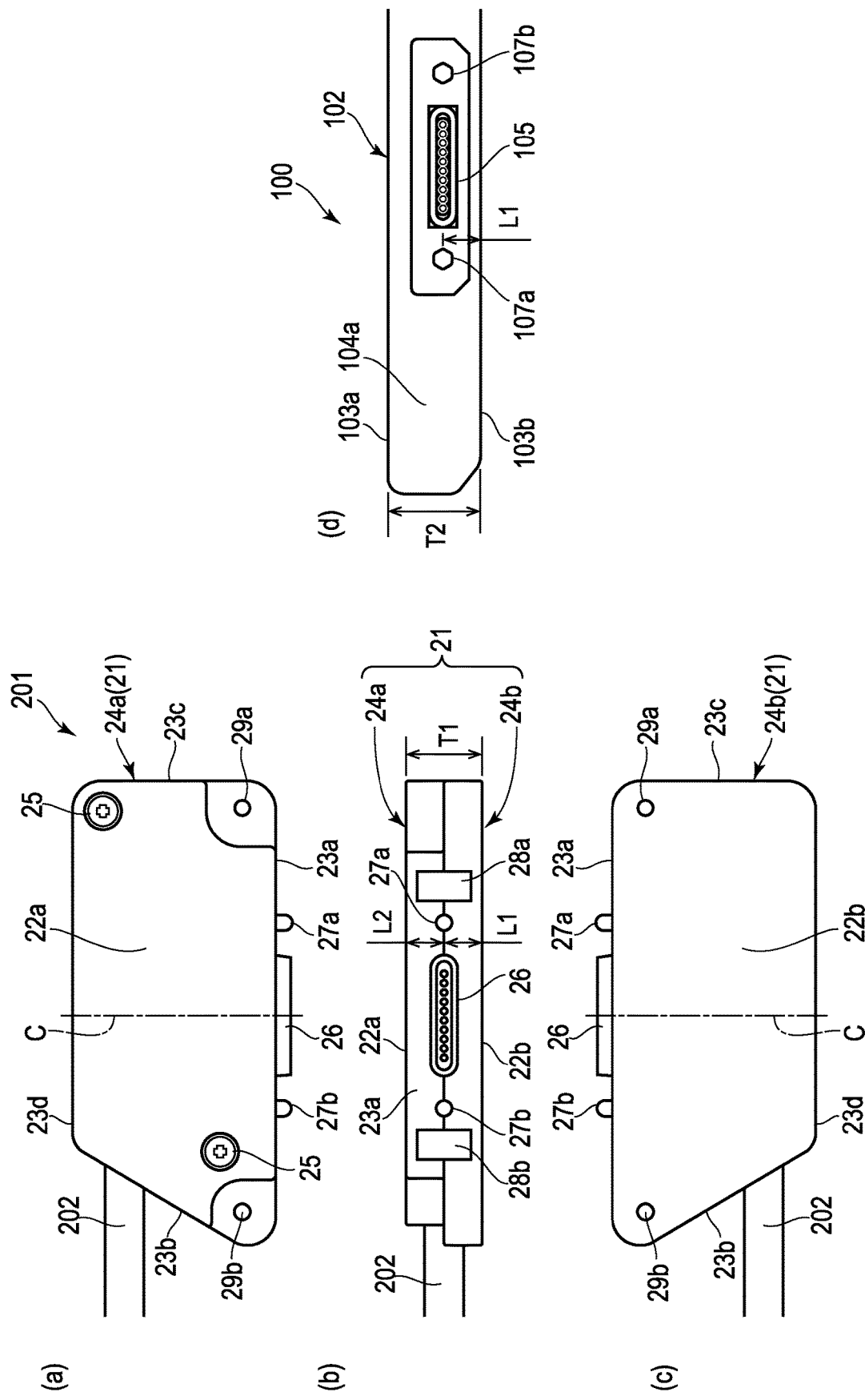

RADIATION IMAGING SYSTEM AND CABLE USED THEREFOR

BACKGROUND OF THE INVENTION

Field of the Invention

The present invention relates to a radiation imaging system and a cable used therefor.

Description of the Related Art

In these years, in the radiation imaging in the medical field, a radiation imaging apparatus is used that includes a flat panel detector (FPD) in which a thin film semiconductor element is arranged on an insulating substrate.

Additionally, in order to enable quick imaging of a wide range of area, a thin, lightweight and portable radiation imaging apparatus is used. Some portable radiation imaging apparatuses include cables for transmitting signals from a controlling apparatus and power from a power source apparatus.

Japanese Patent Application Laid-Open No. 2003-144424 discloses a cassette-type imaging apparatus provided with a connecting portion to which cables can be connected.

Japanese Patent Application Laid-Open No. 2010-259680 discloses a radiation imaging apparatus in which a magnet is installed in a cassette connector for making the connection between a cassette and a cable easy, and a connecting portion of the cassette is connected to the cable with the attractive force of the magnet.

Japanese Patent Application Laid-Open No. 2015-062687 discloses an X-ray imaging system in which a composite connector is fixed to an imaging table side in advance, so as to allow easy cable connection between an external apparatus arranged outside the imaging table and a radiation imaging apparatus.

When fixing a connector to an imaging table, a fixation structure adapted to the shape of the connector is usually required. When the fixation structure is complicated, since the connector cannot be easily fixed to the imaging table, or an extra space for arrangement is needed, it is desirable that the fixation structure is simplified.

One aspect of the present invention aims at simplifying the fixation structure for fixing a connector portion to an imaging table.

SUMMARY OF THE INVENTION

A radiation imaging system according to one aspect of the present invention includes a cable configured to transmit at least one of a signal and power from an external apparatus, a connector portion provided in an end of the cable, a radiation imaging apparatus, and an imaging table, the radiation imaging apparatus being attachable to and removable from the imaging table, wherein the radiation imaging apparatus includes a radiation detecting panel configured to detect radiation and convert the radiation into an electric signal, and a rectangular-shaped housing configured to contain the radiation detecting panel, a housing-side connection terminal portion is arranged in a side surface of the housing, the housing side connection terminal portion is capable to be connected with the connector portion, and the connector portion includes at least one penetrating hole penetrating from a front surface parallel to a radiation incident surface to a rear surface opposite to the front surface, the penetrating hole being usable for fixation to the imaging table.

Further features of the present invention will become apparent from the following description of exemplary embodiments with reference to the attached drawings.

BRIEF DESCRIPTION OF THE DRAWINGS

FIG. 4 is a diagram illustrating an example of the fixation structure of a connector portion according to the first embodiment, and an example of the configuration in the surrounding of a connection terminal portion of the radiation imaging apparatus.

DESCRIPTION OF THE EMBODIMENTS

Preferred embodiments of the present invention will now be described in detail in accordance with the accompanying drawings. Although X-rays are used as radiation in the present embodiment, the present invention is also applicable to an imaging system using gamma rays, proton beams, or the like.

First Embodiment

Figure 1:
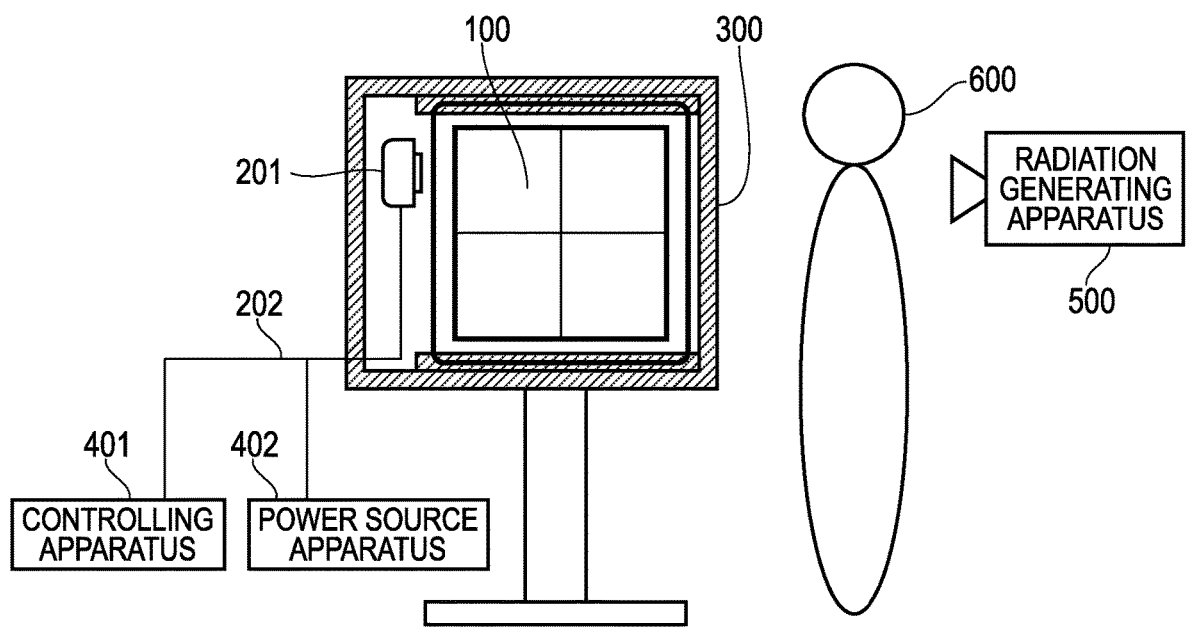
FIG. 1 is a schematic diagram illustrating an example of the schematic configuration of a radiation imaging system according to a first embodiment.

FIG. 1 illustrates an example of the schematic configuration of a radiation imaging system according to the present embodiment.

The radiation imaging system includes a radiation imaging apparatus (hereinafter, the imaging apparatus) 100, a connector portion 201 attachable to and removable from the imaging apparatus 100, and an imaging table 300 that holds the imaging apparatus 100 in an attachable and removable manner.

The imaging apparatus 100 generates radiation image data by detecting the radiation irradiated from a radiation generating apparatus (X-ray generating apparatus) 500 and transmitted through a subject 600, and converting the radiation into an electric signal.

The connector portion 201 enables transmission of a signal between a controlling apparatus 401 and the imaging apparatus 100, and supplies the power from a power source apparatus 402 to the imaging apparatus 100. The connector portion 201 is fixed to an end of a cable 202. The imaging apparatus 100 is electrically and physically connected to external apparatuses, such as the controlling apparatus 401 and the power source apparatus 402, via the cable 202 by the connector portion 201. The imaging apparatus 100 and the connector portion 201 each have a connection terminal portion, which will be described later.

The controlling apparatus 401 transmits, to the imaging apparatus 100, a control signal that instructs power control and drive control of a sensor arranged in the imaging apparatus. The controlling apparatus 401 includes a communication circuit that receives image data from the imaging apparatus 100, an image processing circuit that performs image processing on the received image data, and a display control unit that displays, on a display portion, the data subjected to the image processing. For example, an image display terminal can be used for the controlling apparatus 401.

The power source apparatus 402 supplies power to the imaging apparatus 100.

The cable 202 transmits the signal and power from the external apparatuses to the imaging apparatus 100. The cable 202 includes a signal line that transmits the control signal and the image data, and a power source line used for supplying the power. The cable 202 connects the imaging apparatus 100 to each of the controlling apparatus 401 and the power source apparatus 402. Note that the cable 202 is not limited to be connected to each of the controlling apparatus 401 and the power source apparatus 402, and may be configured to be connected to either one of the controlling apparatus 401 and the power source apparatus 402, and to transmit one of the signal and the power.

Hereinafter, the specific configurations of the imaging apparatus 100, the imaging table 300, and the connector portion 201 will be described.

<Configuration of Imaging Apparatus 100>

Figure 2:
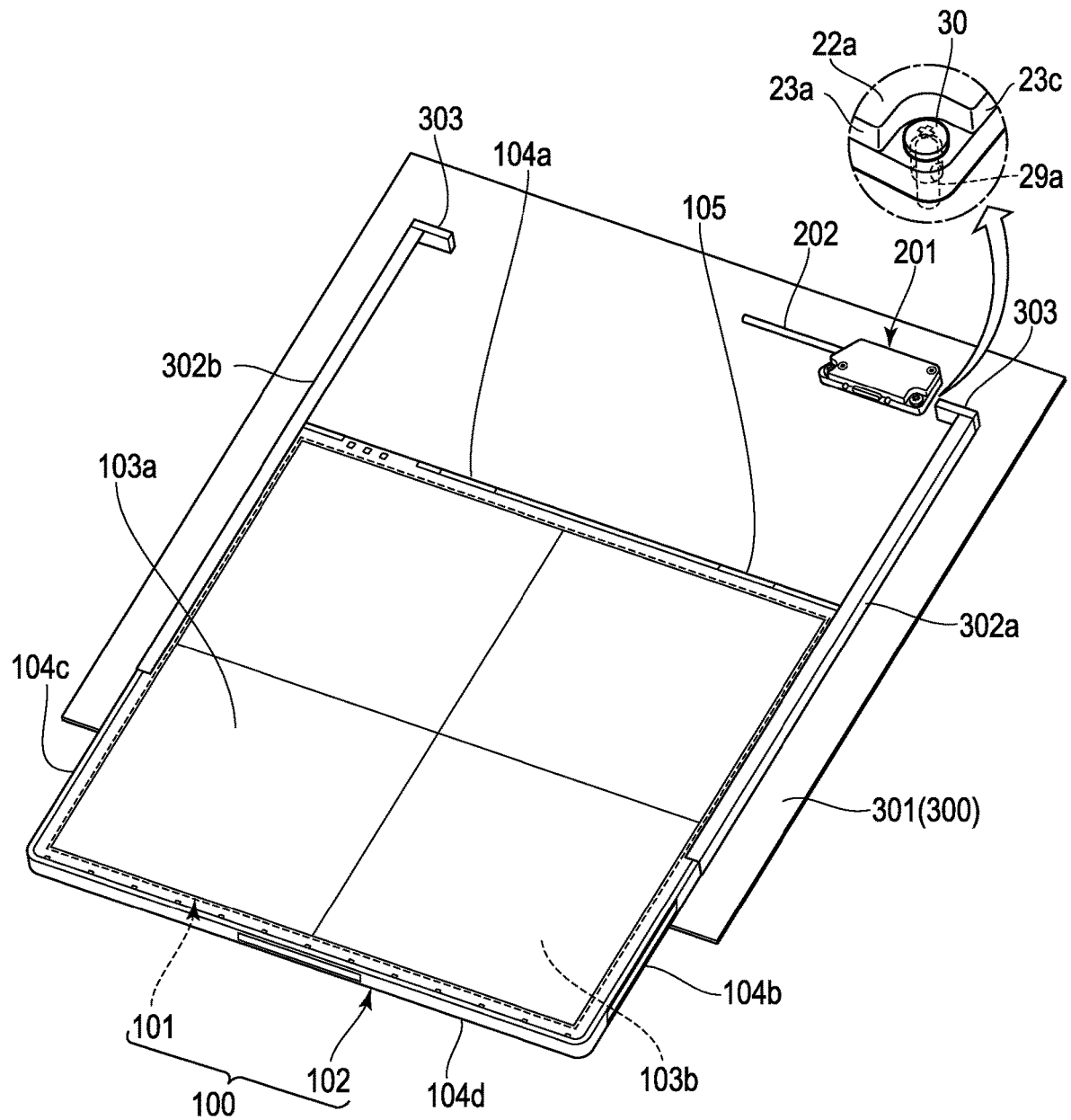
FIG. 2 is a perspective view illustrating an example of the configurations of the radiation imaging apparatus and an imaging table according to the first embodiment.

FIG. 2 illustrates an example of the configurations of the imaging apparatus 100 and the imaging table 300.

The imaging apparatus 100 is portable, and has a thickness within the range of the thickness conforming to the JIS standard (JIS Z4905) for conventional film cassettes. The imaging apparatus 100 includes a radiation detecting panel (hereinafter, the detecting panel) 101 and a housing 102.

The detecting panel 101 is arranged in the housing 102, detects radiation transmitted through the housing 102, and converts the radiation into an electric signal. The detecting panel 101 includes a rectangular-shaped detecting surface.

The housing 102 is the exterior of the imaging apparatus 100, and contains the detecting panel 101. The housing 102 is a generally flat-shaped rectangular parallelepiped, and has a quadrate shape, specifically, a rectangular shape, when seen from a radiation incident surface 103a side. The housing 102 includes a radiation incident surface 103a, an opposing surface 103b opposite to the radiation incident surface 103a, and four side surfaces 104a to 104d. A material, such as CFRP (carbon fiber reinforced plastics), which easily transmits radiation is used for the radiation incident surface 103a. On the other hand, a material, such as an aluminum alloy or a magnesium alloy, having lightweight and high rigidity is used for the opposing surface 103b and the side surfaces 104a to 104d.

The imaging apparatus 100 includes a connection terminal portion (housing-side connection terminal portion) 105 that is electrically and mechanically connected to the connector portion 201, and a wireless communication circuit, and can communicate with the external apparatuses in a wired and wireless manner. The connection terminal portion 105 is provided in the one side surface 104a of the four side surfaces 104a to 104d of the housing 102. The imaging apparatus 100 of the present embodiment is operated according to the control signal from the controlling apparatus 401 as the external apparatus, and the image data obtained by the imaging apparatus 100 is transmitted to the controlling apparatus 401 to perform various kinds of image processing and display processing.

<Configuration of Imaging Table 300>

The imaging table 300 holds the imaging apparatus 100 in an attachable and removable manner. The imaging table 300 includes a substantially plate-like tray 301 for holding the imaging apparatus 100 at a predetermined position thereinside.

Guide rails 302a and 302b as guiding portions, stopper portions 303, and the connector portion 201 are fixed to the tray 301. The guide rails 302a and 302b guide the side surfaces 104b and 104c, which are adjacent to the side surface 104a of the housing 102 of the imaging apparatus 100 where the connection terminal portion 105 is arranged, along a longitudinal direction. The stopper portions 303 are arranged in one ends of the both ends of the guide rails 302a and 302 in the longitudinal direction, and regulate sliding of the imaging apparatus 100 along the guide rails 302a and 302b. Additionally, the connector portion 201 is fixed to the tray 301 at a position close to the one ends of the both ends of the guide rails 302a and 302b in the longitudinal direction by using a fixation structure, which will be described later.

When an examiner (user) inserts and slides the imaging apparatus 100 into the guide rails 302a and 302b from the other ends side of the guide rails 302a and 302b in the longitudinal direction, the side surfaces 104b and 104c are guided by the guide rails 302a and 302b. When the examiner slides the imaging apparatus 100 along the guide rails 302a and 302b until the imaging apparatus 100 abuts the stopper portions 303, the connection terminal portion 105 of the imaging apparatus 100 is connected to the connector portion 201. On the other hand, when the examiner slides the imaging apparatus 100 toward the other ends side of the guide rails 302a and 302b in the longitudinal direction, and removes the imaging apparatus 100 from the guide rails 302a and 302b, the connection terminal portion 105 can be removed from the connector portion 201.

In this manner, since attachment to and removable from the connector portion 201 can be performed simultaneously with insertion and removal of the imaging apparatus 100, respectively, and the examiner does not need to separately perform operations of attaching and removing of the connector portion 201, the work efficiency can be improved.

Note that, although the imaging table 300 illustrated in FIG. 1 is a standing imaging table with which the radiation incident surface 103a of the imaging apparatus 100 is along the vertical direction, the imaging table 300 may be a table-type imaging table with which the radiation incident surface 103a is along the horizontal direction.

<Configuration of Connector Portion 201>

The connector portion 201 functions as a communication channel for communicating between the imaging apparatus 100 (the counterpart apparatus) and the controlling apparatus 401, and functions as a supply channel for supplying the power from the power source apparatus 402 to the imaging apparatus 100. The connector portion 201 is fixed to the end of the cable 202. The connector portion 201 is attachable to and removable from the connection terminal portion 105 of the imaging apparatus 100. The connector portion 201 is fixed to the tray 301 with the fixation structure, so as to be connected to the imaging apparatus 100 when the imaging apparatus 100 is loaded onto the imaging table 300. The connector portion 201 is arranged such that a connector-side connection terminal portion 26 is parallel with the stopper portions 303.

<Fixation Structure of Connector Portion 201>

Figure 3:
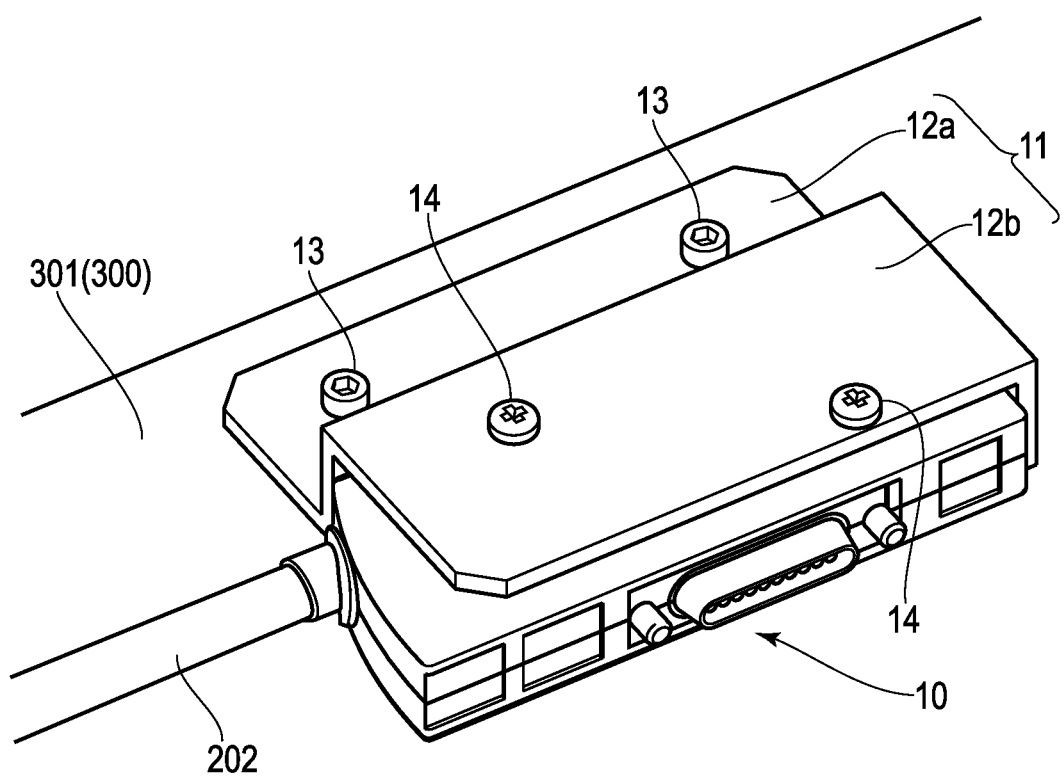
FIG. 3 is a perspective view illustrating an example of the fixation structure of a connector portion of a comparison example.

Here, the fixation structure of the connector portion 201 according to the present embodiment will be described in contrast to a comparison example illustrated in FIG. 3. FIG. 3 illustrates an example of the fixation structure of a connector portion 10 of the comparison example.

The fixation structure of the comparison example is a configuration in which the connector portion 10 is fixed to the tray 301 by using a fixture 11. The fixture 11 includes a first fixing portion 12a fixed to the tray 301, and a second fixing portion 12b fixed to the connector portion 10. The first fixing portion 12a is fixed to the tray 301 by fastening fastening members 13 to the tray 301 through penetrating holes of the first fixing portion 12a. On the other hand, the second fixing portion 12b is fixed to the connector portion 10 by fixing fastening members 14 to the connector portion 10 through penetrating holes of the second fixing portion 12b. In this manner, the connector portion 10 is indirectly fixed to the tray 301 via the fixture 11. In the comparison example, since the fixture 11 is needed, the fixation structure cannot be simplified. Additionally, since the space for arranging the first fixing portion 12a on the tray 301 is needed in order to overlap the first fixing portion 12a of the fixture 11 with the tray 301 and to fix the first fixing portion 12a of the fixture 11 to the tray 301, downsizing cannot be achieved.

(a) to (c) in FIG. 4 illustrate an example of the fixation structure of the connector portion 201 according to the present embodiment. (a) in FIG. 4 is a plan view of the connector portion 201, (b) in FIG. 4 is a side view of the connector portion 201, and (c) in FIG. 4 is a rear view of the connector portion 201.

The connector portion 201 includes a case 21, the connection terminal portion (the connector-side connection terminal portion) 26, regulation pins 27a and 27b, and holding portions 28a and 28b.

The case 21 is the exterior of the connector portion 201, and contains each component of the connector portion 201. The case 21 has a generally flat-shape, and has a quadrate shape, specifically, a right-angle trapezoid shape (substantially trapezoid shape) when seen in one of plan view and rear view. The case 21 includes a front surface (a first surface) 22a, a rear surface (a second surface) 22b opposite to the front surface 22a, and a plurality of (here, four) side surfaces 23a to 23d. In a state where the connector portion 201 is fixed to the tray 301, and the connection terminal portion 26 of the connector portion 201 is connected to the connection terminal portion 105 of the imaging apparatus 100, the front surface 22a of the case 21 is parallel to the radiation incident surface 103a of the imaging apparatus 100.

Additionally, the case 21 includes a first case 24a having the first surface 22a, and a second case 24b having the rear surface 22b, and the first case 24a and the second case 24b are united by a fastening member 25. The cable 202 is connected and fixed to the one side surface 23b of the four side surfaces 23a to 23d. The side surface 23b is a surface that is adjacent to the side surfaces 23a at an acute angle, and that is adjacent to the side surface 23d at an obtuse angle.

The connection terminal portion 26 is connected to the connection terminal portion 105 of the imaging apparatus 100, in order to enable transmission of signals between the imaging apparatus 100 and the controlling apparatus 401, and to supply the power to the imaging apparatus 100. The connection terminal portion 26 is provided in the one side surface 23a of the four side surfaces 23a to 23d of the case 21, and is located at the center of a thickness T1 from the front surface 22a to the rear surface 22b of the housing 102. The connection terminal portion 26 is located so as to be opposite to the connection terminal portion 105 of the imaging apparatus 100.

The regulation pins 27a and 27b regulate the movement of the imaging apparatus 100, when the imaging apparatus 100 tries to move in a direction parallel to the side surface 23a in a state where the connection terminal portion 26 is connected to the connection terminal portion 105 of the imaging apparatus 100. Since the regulation pins 27a and 27b regulate the movement of the imaging apparatus 100, the connection terminal portion 26 can be prevented from receiving an excessive load. The regulation pins 27a and 27b are located away from each other on both sides across the connection terminal portion 26 of the side surface 23a. The regulation pins 27a and 27b mate with regulated portions 107a and 107b, which will be described later, of the imaging apparatus 100, in a state where the connection terminal portion 26 is connected to the connection terminal portion 105 of the imaging apparatus 100.

The holding portions 28a and 28b hold the imaging apparatus 100 to be in the state where the connection terminal portion 26 is connected to the connection terminal portion 105 of the imaging apparatus 100. The holding portions 28a and 28b are located away from each other on both sides across the connection terminal portion 26 and the regulation pins 27a and 27b of the side surface 23a. The holding portions 28a and 28b include, for example, magnets, and are attracted to a magnetic body of the imaging apparatus 100. The magnetic body of the imaging apparatus 100 may be, for example, a metal included in the housing 102, or may be a metal provided on the side surface 104a of the housing 102.

Here, the case 21 of the connector portion 201 according to the present embodiment is configured to allow direct fixation to the tray 301. Specifically, the case 21 includes penetrating holes 29a and 29b penetrating from the front surface 22a to the rear surface 22b. The penetrating holes 29a and 29b are located in corner portions of the cases 21 that are adjacent to each other. Additionally, the penetrating holes 29a and 29b are located in the corner portions close to the side surface 23a in which the connection terminal portion 26 is arranged among the four side surfaces 23a to 23d of the case 21. Specifically, the penetrating hole 29a is located close to the corner portion where the side surface 23a and the side surface 23c intersect, and the penetrating hole 29b is located close to the corner portion where the side surface 23a and the side surface 23b intersect.

As illustrated in an enlarged perspective view in FIG. 2, the connector portion 201 is fixed to the tray 301 by inserting fastening members 30 into the penetrating holes 29a and 29b, and fastening the fastening members 30 to holes, which are not illustrated, of the tray 301. In this manner, the connector portion 201 includes the penetrating holes 29a and 29b, and thus the connector portion 201 can be directly fixed to the tray 301, which makes it unnecessary to use the fixture as in the comparison example. Therefore, the fixation structure of the connector portion 201 can be simplified. Additionally, since the connector portion 201 includes the penetrating holes 29a and 29b, the space for arranging the fixture is not needed as in the comparison example. Therefore, space-saving can be achieved.

Additionally, the front surface 22a of the case 21 has a shape in which the corner portion where the side surface 23a and the side surface 23b intersect, and the corner portion where the side surface 23a and the side surface 23c intersect are lowered by one step toward the rear surface 22b side, and the penetrating holes 29a and 29b are formed in the respective corner portions. That is, the surroundings of the penetrating holes 29a and 29b on the front surface 22a side are formed to be one step lower. In this manner, by making the surroundings of the penetrating holes 29a and 29b on the front surface 22a side one step lower, when the fastening members 30 are inserted into the penetrating holes 29a and 29b, the fastening members 30 can be suppressed from protruding in the thickness direction of the case 21, and the thickness of the tray 301 can be reduced. Note that, although the surroundings of the penetrating holes 29a and 29b on the front surface 22a side are opened toward the side surfaces 23a, 23b and 23c sides as illustrated in (a) in FIG. 4, and (b) in FIG. 4, the surroundings of the penetrating holes 29a and 29b are not limited to this case, and may be so-called counterbore surfaces that are not opened toward the side surfaces 23a, 23b and 23c sides.

Note that the connector portion 201 may be fixed to a predetermined position on the imaging table 300 side, and is not limited to the case where the connector portion 201 is fixed to the tray 301. Additionally, recently, since imaging apparatuses conforming to the external shape dimension in the film cassette has become widespread, versatile imaging tables that can correspond to various imaging apparatuses with slight modifications have been provided from various manufactures. According to the fixation structure of the connector portion 201 of the present embodiment, since simplification and space-saving are achieved, the connector portion 201 can be fixed to imaging tables provided from various manufactures only with minimum improvements.

Additionally, when seen from a direction perpendicular to one of the front surface 22a and the rear surface 22b as illustrated in (a) in FIG. 4 and (c) in FIG. 4, the penetrating holes 29a and 29b of the case 21 are arranged at symmetric positions about a center line C of a width direction of the connection terminal portion 26. Here, a case of specification is assumed where the connector portion 201 is electrically and mechanically connectable to the connection terminal portion 105 of the imaging apparatus 100, in a state where the connector portion 201 is inverted by 180 degrees, i.e., a state where the case 21 is inverted so as to reverse the front surface 22a and the rear surface 22b. In this case, since the penetrating holes 29a and 29b are at symmetric positions with respect to the connection terminal portion 26, even when the connector portion 201 is inverted by 180 degrees, the fastening members 30 can be inserted into the penetrating holes 29a and 29b, and fastened to the same holes of the tray 301 that are used for fastening before inverting. Accordingly, even when the connector portion 201 is inverted for changing the direction from which the cable 202 is drawn, it can be easily handled. Note that the surroundings of the penetrating holes 29a and 29b on the rear surface 22b side may also be formed to be one step lower, or counterbore surfaces may be formed also on the rear surface 22b side. By doing so, even when the connector portion 201 is inverted by 180 degrees, and the fastening members 30 are inserted into the penetrating holes 29a and 29b, the fastening members 30 can be suppressed from protruding in the thickness direction of the case 21.

Note that (d) in FIG. 4 illustrates an example of the configuration of the surrounding of the connection terminal portion 105 of the imaging apparatus 100. The imaging apparatus 100 includes, on the side surface 104a of the housing 102, the connection terminal portion 105, and the regulated portions 107a and 107b that are away from each other on both sides across the connection terminal portion 105. The housing 102 of the imaging apparatus 100 has a thickness T2 from the radiation incident surface 103a to the opposing surface 103b. Here, as illustrated in (b) in FIG. 4 and (d) in FIG. 4, the thickness T1 of the connector portion 201 is equal to or less than the thickness T2 of the imaging apparatus 100. Additionally, as illustrated in (d) in FIG. 4, the connection terminal portion 105 is not located at the center of the thickness T2 of the housing 102, but is located offset to the opposing surface 103b side from the center of the thickness T2. At this time, a thickness L1 from the center of the connection terminal portion 26 to the rear surface 22b of the connector portion 201 is the same as a thickness L1 from the connection terminal portion 105 to the opposing surface 103b of the imaging apparatus 100. Accordingly, by sliding the imaging apparatus 100 along the guide rails 302a and 302b, the connection terminal portion 105 of the imaging apparatus 100 can be connected to the connection terminal portion 26 of the connector portion 201 fixed to the tray 301.

Further, a thickness L2 from the center of the connection terminal portion 26 to the front surface 22a of the connector portion 201 is the same as the thickness L1 from the connection terminal portion 105 to the opposing surface 103b of the imaging apparatus 100. Accordingly, even when the connector portion 201 is inverted by 180 degrees and is fixed to the tray 301, the connection terminal portion 105 of the imaging apparatus 100 can be connected to the connection terminal portion 26 of the connector portion 201 fixed to the tray 301.

As described above, according to the present embodiment, the connector portion 201 includes the penetrating holes 29a and 29b, which can be used for fixation to the imaging table 300, penetrating from the front surface 22a which is parallel to the radiation incident surface 103a to the rear surface 22b opposite to the front surface 22a. In this manner, since the connector portion 201 includes the penetrating holes 29a and 29b, the connector portion 201 can be directly fixed to the tray 301. Therefore, the fixation structure of the connector portion 201 can be simplified. Additionally, since the penetrating holes 29a and 29b are located in the corner portions of the case 21, the connector portion 201 can be firmly fixed to the tray 301. In addition, since the penetrating holes 29a and 29b are located in the corner portions close to the side surface 23a in which the connection terminal portion 26 is provided among the four side surfaces 23a to 23d of the case 21, the connector portion 201 can be further firmly fixed to the tray 301.

Note that, although the case has been described where the connector portion 201 includes the two penetrating holes 29a and 29b in the present embodiment, the connector portion 201 is not limited to this case, and may include one penetrating hole, or may include three or more penetrating holes. Additionally, each of three corner portions or four corner portions of the case 21 may include a penetrating hole.

Second Embodiment

Figure 5A:
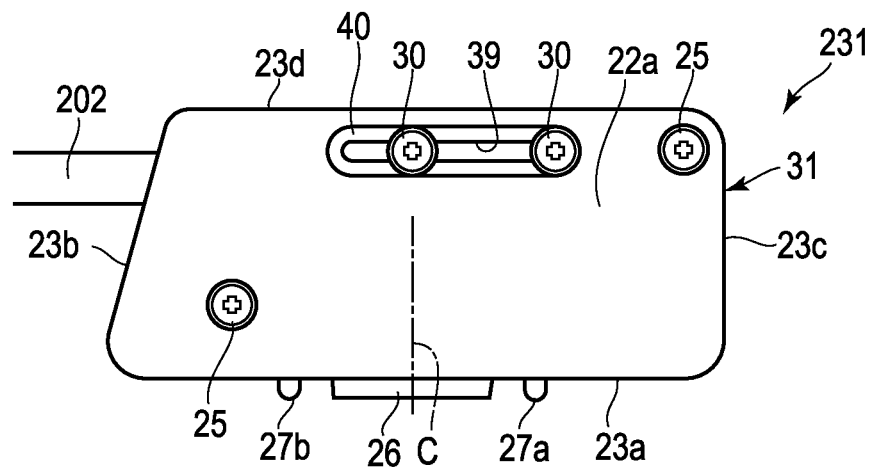
FIG. 5A is a plan view illustrating an example of the fixation structure of a connector portion according to a second embodiment.
Figure 5B:
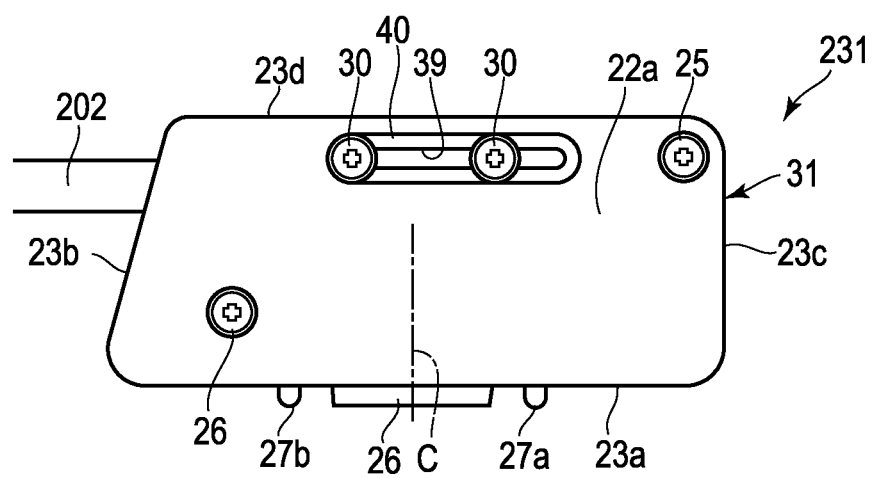
FIG. 5B is a plan view illustrating the example of the fixation structure of the connector portion according to the second embodiment.

FIG. 5A and FIG. 5B illustrate an example of the configuration of a connector portion 231 of a second embodiment. Note that the same configurations as those in the first embodiment will be denoted by the same numerals, and a description will be omitted where appropriate.

A case 31 includes a penetrating hole 39 penetrating from the front surface 22a to the rear surface. The connector portion 231 is fixed to the tray 301 by inserting the fastening members 30 into the penetrating hole 39 and fastening the fastening members 30 to holes, which are not illustrated, of the tray 301.

The penetrating hole 39 according to the present embodiment is a long hole that is long along a direction perpendicular to the direction in which the connection terminal portion 105 of the imaging apparatus 100 is connected to the connection terminal portion 26 of the connector portion 231, in other words, a long hole that is long in the direction along the width direction of the connection terminal portion 26. Accordingly, as illustrated in FIG. 5A and FIG. 5B, the position of the connector portion 231 can be adjusted in the direction along the width direction of the connection terminal portion 26 with respect to the tray 301, without changing the positions at which the fastening members 30 are fastened to the holes of the tray 301. In this manner, by adjusting the position of the connector portion 231, even for the imaging apparatus 100 with a different position of the connection terminal portion 105, the position of the connection terminal portion 26 of the connector portion 231 can be aligned with the position of the connection terminal portion 105 of the imaging apparatus 100.

Additionally, since a counterbore surface 40 is formed along the long hole in the surrounding of the front surface 22a side of the penetrating hole 39 to be one step lower, the fastening members 30 can be suppressed from protruding in the thickness direction of the case 31. Note that a counterbore surface is not limited to the front surface 22a side of the penetrating hole 39, and may be also formed along the long hole in the surrounding of the rear surface 22b side to be one step lower. By doing so, even when the connector portion 231 is inverted by 180 degrees, and the fastening members 30 are inserted into the penetrating hole 39, the fastening members 30 can be suppressed from protruding in the thickness direction of the case 31.

According to the above-described embodiments of the present invention, the fixation structure for fixing the connector portion to the imaging table can be simplified.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-043774, filed Mar. 17, 2021, which is hereby incorporated by reference herein in its entirety.

What is claimed is:

1. A radiation imaging system, comprising:
a cable configured to transmit at least one of a signal and power from an external apparatus;
a connector portion provided in an end of the cable;
a radiation imaging apparatus, said radiation imaging apparatus including a radiation detecting panel configured to detect X-ray radiation, a rectangular-shaped housing configured to contain the radiation detecting panel, and a housing-side connection terminal portion arranged in a side surface of the housing, said housing-side connection terminal being capable of being connected with the connector portion; and
an imaging table, the radiation imaging apparatus being attachable to and removable from the imaging table,
wherein the connector portion includes at least one slotted hole penetrating from a front surface parallel to a radiation incident surface of the radiation detecting panel to a rear surface opposite to the front surface and extending in a predetermined direction, the predetermined direction being orthogonal to the attaching/detaching direction of the connector portion to the housing-side connection terminal portion and orthogonal to the penetration direction, the slotted hole being usable for fixation to the imaging table.

2. A radiation imaging system according to claim 1, wherein the connector portion includes a flat-shaped case, and
the slotted hole is located in a corner portion of the case.

3. A radiation imaging system according to claim 2, wherein the connector portion includes, in one side surface of a plurality of side surfaces of the case, a connector-side connection terminal portion connected with the housing-side connection terminal portion, and
the slotted hole is located in a corner portion of the case close to the side surface in which the connector-side connection terminal portion is provided among the plurality of side surfaces.

4. A radiation imaging system according to claim 3, wherein the imaging table includes a tray, and a guide rail and a stopper portion fixed to the tray, and
the tray, the guide rail and the stopper portion are configured to be used for mounting the radiation imaging apparatus.

5. A radiation imaging system according to claim 4, wherein the connector portion is arranged such that the connector-side connection terminal portion is parallel to the stopper portion.

6. A radiation imaging system according to claim 1, wherein the connector portion includes a connector-side connection terminal portion located at a center of a thickness direction from the front surface to the rear surface, and
a thickness from the connector-side connection terminal portion to one of the front surface and the rear surface is the same as a thickness from the housing-side connection terminal portion to an opposing surface opposite to the radiation incident surface.

7. A radiation imaging system according to claim 1, wherein a thickness of the connector portion from the front surface to the rear surface is equal to or less than a thickness of the housing.

8. A cable configured for use in a radiation imaging system comprising an external apparatus, a radiation imaging apparatus configured to detect X-ray radiation, said radiation imaging apparatus including a rectangular-shaped housing configured to contain a radiation detecting panel and a housing-side connection terminal portion arranged in a side surface of the housing, and an imaging table, the radiation imaging apparatus being attachable to and removable from the imaging table, the cable configured to transmit at least one of a signal and power from the external apparatus to the radiation imaging apparatus, the cable comprising:
a connector portion arranged in an end of the cable, and including at least one slotted hole penetrating from a front surface parallel to a radiation incident surface of the radiation imaging apparatus to a rear surface opposite to the front surface and extending in a predetermined direction, the predetermined direction being orthogonal to the attaching/detaching direction of the connector portion to the housing-side connection terminal portion and orthogonal to the penetration direction, the slotted hole being usable for fixation to the imaging table.

9. A cable according to claim 8, wherein the connector portion includes a flat-shaped case, and
the slotted hole is located in a corner portion of the case.

10. A cable according to claim 9, wherein the connector portion includes, in one side surface of a plurality of side surfaces of the case, a connector-side connection terminal portion connected with the housing-side connection terminal portion, and
the slotted hole is located in a corner portion of the case close to the side surface in which the connector-side connection terminal portion is provided among the plurality of side surfaces.

11. A cable according to claim 10, wherein the imaging table includes a tray, and a guide rail and a stopper portion fixed to the tray, and the tray, the guide rail and the stopper portion are configured to be used for mounting the radiation imaging apparatus.

12. A cable according to claim 11, wherein the connector portion is arranged such that the connector-side connection terminal portion is parallel to the stopper portion.

13. A cable according to claim 8, wherein the connector portion includes a connector-side connection terminal portion located at a center of a thickness direction from the front surface to the rear surface, and a thickness from the connector-side connection terminal portion to one of the front surface and the rear surface is the same as a thickness from the housing-side connection terminal portion to an opposing surface opposite to the radiation incident surface.

14. A cable according to claim 8, wherein a thickness of the connector portion from the front surface to the rear surface is equal to or less than a thickness of the housing.

* * * * *